United States Patent
Chelnokov et al.

(10) Patent No.: US 12,182,962 B2
(45) Date of Patent: *Dec. 31, 2024

(54) COMPRESSION OF CT RECONSTRUCTION IMAGES

(71) Applicant: James R. Glidewell Dental Ceramics, Inc., Newport Beach, CA (US)

(72) Inventors: Fedor Chelnokov, Khimki (RU); Grant Karapetyan, Moscow (RU)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/456,215

(22) Filed: Aug. 25, 2023

(65) Prior Publication Data

US 2023/0419441 A1    Dec. 28, 2023

Related U.S. Application Data

(63) Continuation of application No. 17/107,126, filed on Nov. 30, 2020, now Pat. No. 11,741,569.

(51) Int. Cl.
*G06T 3/40*    (2024.01)
*G06T 11/00*   (2006.01)
*A61B 6/03*    (2006.01)

(52) U.S. Cl.
CPC .............. *G06T 3/40* (2013.01); *G06T 11/008* (2013.01); *A61B 6/032* (2013.01); *G06T 2200/04* (2013.01); *G06T 2210/41* (2013.01)

(58) Field of Classification Search
CPC ..... G06T 3/40; G06T 11/008; G06T 2200/04; G06T 2210/41; A61B 6/032; A61B 6/5205

See application file for complete search history.

(56) References Cited

U.S. PATENT DOCUMENTS

| 6,111,974 A * | 8/2000 | Hiraoglu .................. G06T 7/11 250/363.04 |
| 2005/0135664 A1* | 6/2005 | Kaufhold .............. G06T 11/006 382/131 |

(Continued)

OTHER PUBLICATIONS

SaanaJ enu; Feasibility Study of a Geant4-based Diagnostic X-ray Dose Simulator; Licentiate of Philosophy Thesis Medical Physics Materials Research and Nanosciences; May 4, 2019 . (Year: 2019).*

(Continued)

*Primary Examiner* — Michael Le
(74) *Attorney, Agent, or Firm* — Klarquist Sparkman, LLP

(57) ABSTRACT

A computer-implemented method and system compresses CT reconstruction images and can include: receiving a volumetric density file including one or more voxels; replacing one or more voxel density values below an air density value with the air density value; replacing one or more voxel density values above a material density value with the material density value; determining one or more voxels of interest; replacing one or more non-interesting voxel density values below a material surface density with the air density value; replacing one or more non-interesting voxel density values above the material surface density with the material density value; quantizing all voxels to provide a reduced volume image; and compressing the reduced volume image to provide a compressed volume image.

20 Claims, 10 Drawing Sheets

(56) References Cited

U.S. PATENT DOCUMENTS

| | | | |
|---|---|---|---|
| 2006/0088198 A1* | 4/2006 | Arnold | G06T 7/0012 |
| | | | 382/131 |
| 2009/0169081 A1* | 7/2009 | Garms | G06T 7/62 |
| | | | 382/131 |
| 2018/0028064 A1* | 2/2018 | Elbaz | G06T 7/75 |
| 2019/0287273 A1* | 9/2019 | Yokose | G06T 15/08 |
| 2020/0242761 A1* | 7/2020 | Butler | G06T 7/0012 |

OTHER PUBLICATIONS

Cynthia H. McCollough, Shuai Leng, Lifeng Yu, Joel G. Fletcher: Dual- and Multi-Energy CT :Principles, Technical Approaches, and Clinical Applications; Radiology.Sep. 2015; 276(3): 637-653. (Year: 2015).*

* cited by examiner

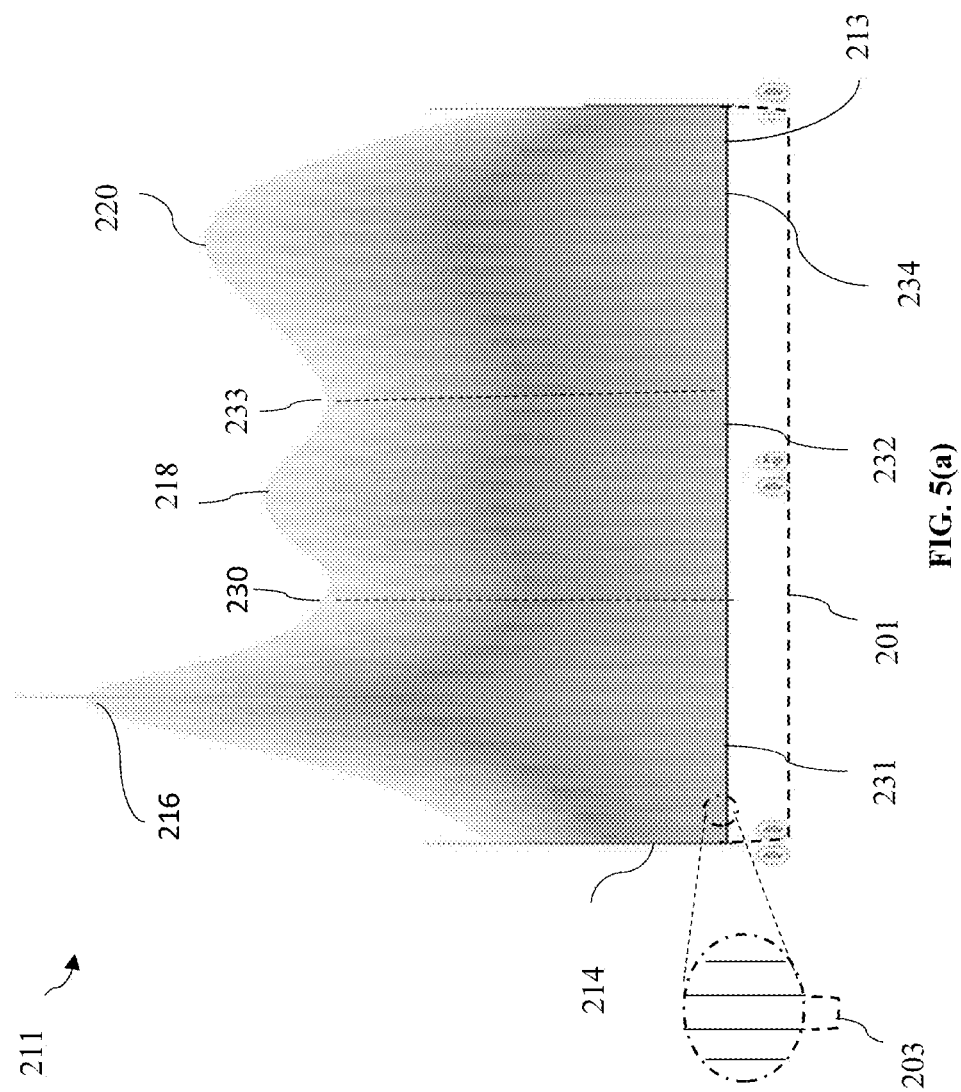

COMPRESSION OF CT RECONSTRUCTION IMAGES

CROSS-REFERENCE TO RELATED APPLICATIONS

This application is a continuation of U.S. patent application Ser. No. 17/107,126 filed on Nov. 30, 2020, which is herein incorporated by reference in its entirety.

BACKGROUND

Computed Tomography X-ray scanners ("CT scanners") typically produce projection images which are tomographically reconstructed by software that generates a volumetric density file containing density information at a particular location based on the material density detected at the particular location. For example, an object can have density greater than air, so that regions where the material is present have higher density values in the corresponding location in the volumetric density file than regions where air is present. The volumetric density file can be provided to Computer Aided Design ("CAD") and Computer Aided Manufacturing ("CAM") software, which can extract a digital surface.

Conventional volumetric density files typically form a three dimensional grid and are very large in size. For example, a three dimensional grid can have dimensions of 2000×2000×2000 voxels. This can create very large volumetric density files. For example, in the format where each voxel is represented with a 16-bit value, the volumetric density file can take 16 Gb of storage space.

The large volumetric density file sizes can limit the number of files that can fit on a particular storage device. The large volumetric density file sizes can also limit its portability, since such large files can prohibit fast transfer of the volumetric density file to another machine or location. This can limit processing of volumetric density files to a few local machines for generating the digital model and surface mesh.

SUMMARY

A computer-implemented method of compressing CT reconstruction images can include: receiving a volumetric density file including one or more voxels; replacing one or more voxel density values below an air density value with the air density value; replacing one or more voxel density values above a material density value with the material density value; determining one or more voxels of interest; replacing one or more non-interesting voxel density values below a material surface density with the air density value; replacing one or more non-interesting voxel density values above the material surface density with the material density value; quantizing all voxels to provide a reduced volume image; and compressing the reduced volume image to provide a compressed volume image.

A system of compressing CT reconstruction images, can include: a processor; a computer-readable storage medium including instructions executable by the processor to perform steps including: receiving a volumetric density file including one or more voxels; replacing one or more voxel density values below an air density value with the air density value; replacing one or more voxel density values above a material density value with the material density value; determining one or more voxels of interest; replacing one or more non-interesting voxel density values below a material surface density with the air density value; replacing one or more non-interesting voxel density values above the material surface density with the material density value; quantizing all voxels to provide a reduced volume image; and compressing the reduced volume image to provide a compressed volume image.

A non-transitory computer readable medium storing executable computer program instructions for compressing CT reconstruction images, the computer program instructions including instructions for: receiving a plurality of radiographs; and determining an axis of rotation per scan from the plurality of radiographs prior to CT reconstruction; receiving a volumetric density file including one or more voxels; replacing one or more voxel density values below an air density value with the air density value; replacing one or more voxel density values above a material density value with the material density value; determining one or more voxels of interest; replacing one or more non-interesting voxel density values below a material surface density with the air density value; replacing one or more non-interesting voxel density values above the material surface density with the material density value; quantizing all voxels to provide a reduced volume image; and compressing the reduced volume image to provide a compressed volume image.

BRIEF DESCRIPTION OF THE DRAWINGS

FIG. 5(a) and FIG. 5(b) show examples of histograms in some embodiments.

DETAILED DESCRIPTION

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

Figure 1:
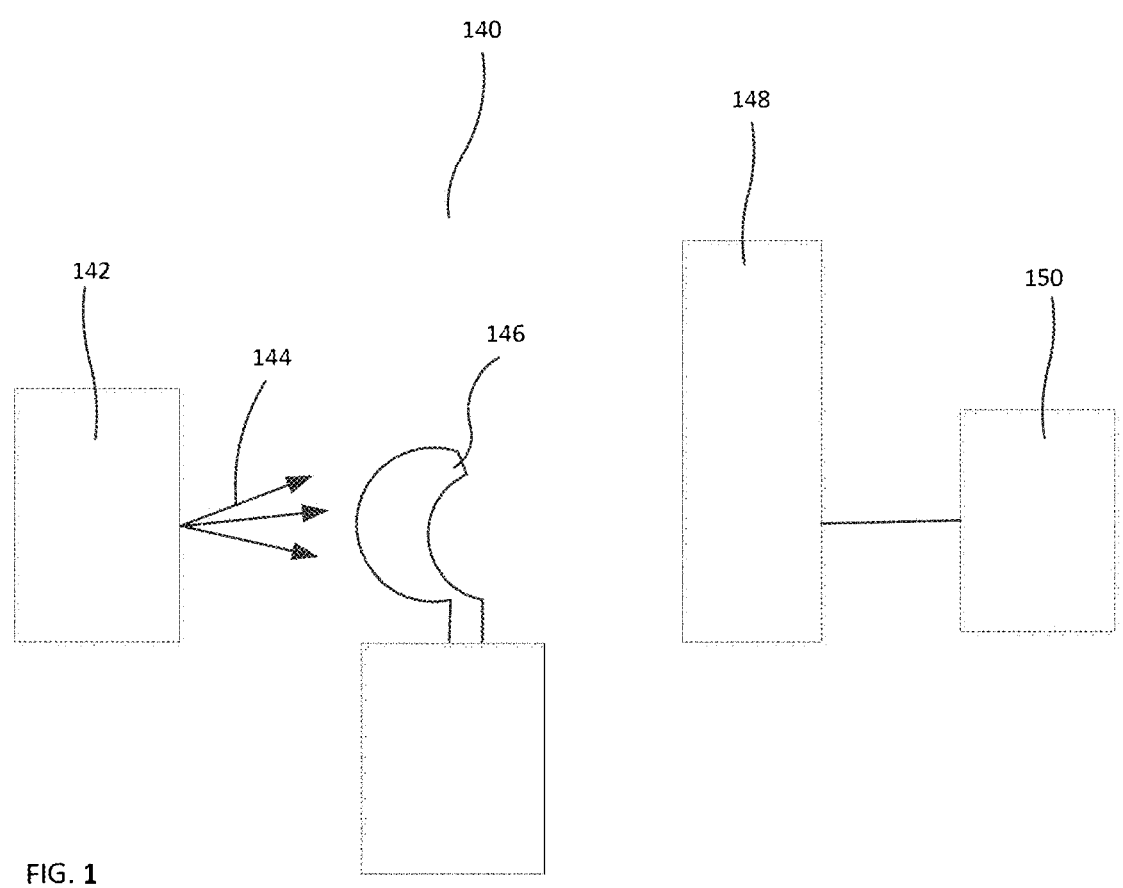
FIG. 1 shows a schematic diagram of a computed tomography (CT) scanning system.

A computed tomography (CT) scanner uses x-rays to make a detailed image of an object. A plurality of such images are then combined to form a 3D model of the object. A schematic diagram of an example of a CT scanning system 140 is shown in FIG. 1. The CT scanning system 140 includes a source of x-ray radiation 142 that emits an x-ray beam 144. An object 146 being scanned is placed between the source 142 and an x-ray detector 148. In some embodiments, the object can be any object that can, for example, fit in a CT scanning system and be penetrated by x-rays. The x-ray detector 148, in turn, is connected to a processor 150 that is configured to receive the information from the detector 148 and to convert the information into a digital image file. Those skilled in the art will recognize that the processor 150 may comprise one or more computers that may be directly connected to the detector, wirelessly connected, connected via a network, or otherwise in direct or indirect communication with the detector 148.

An example of a suitable scanning system 140 includes a Nikon Model XTH 255 CT Scanner (Metrology) which is commercially available from Nikon Corporation. The example scanning system includes a 225 kV microfocus x-ray source with a 31 μm focal spot size to provide high performance image acquisition and volume processing. The processor 150 may include a storage medium that is configured with instructions to manage the data collected by the scanning system. A particular scanning system is described for illustrative purposes; any type/brand of CT scanning system can be utilized.

Figure 2:
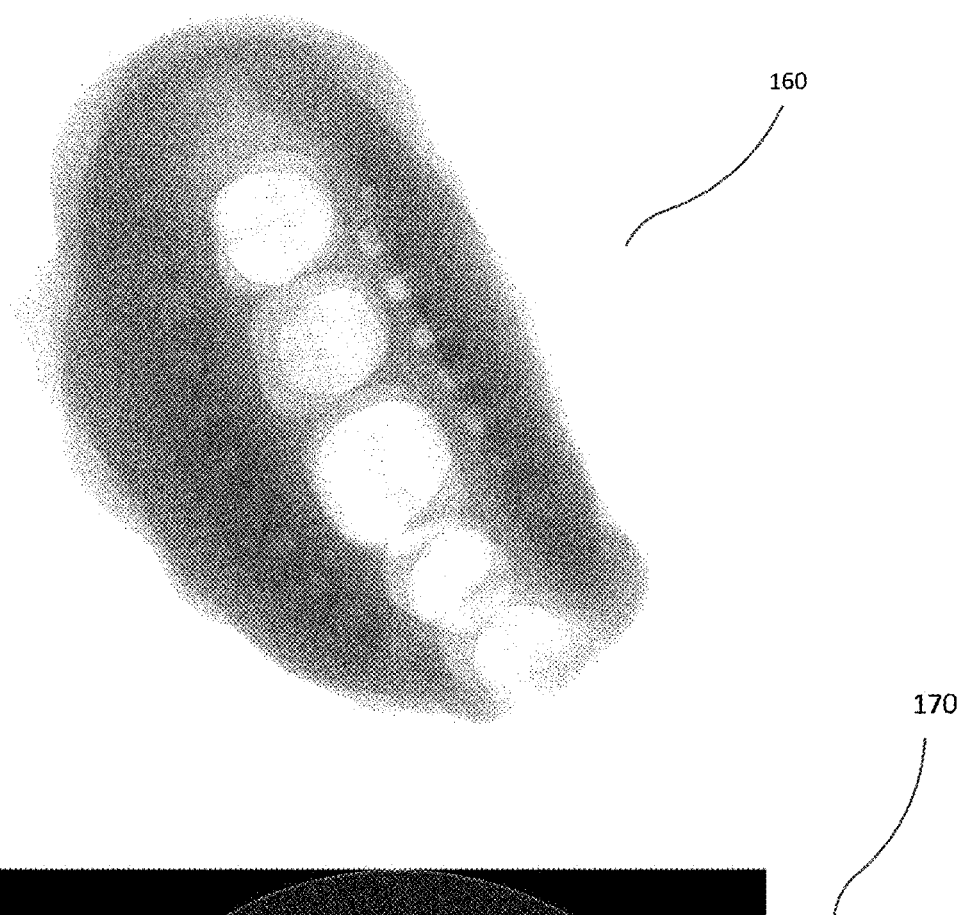
FIG. 2 shows a 2-dimensional (2D) radiographic image of a dental impression tray containing a dental impression.

One example of CT scanning is described in U.S. Patent Application No. US20180132982A1 to Nikolskiy et al., which is hereby incorporated in its entirety by reference. As noted above, during operation of the scanning system 140, the object 146 is located between the x-ray source 142 and the x-ray detector 148. A series of images of the object 146 are collected by the processor 150 as the object 146 is rotated in place between the source 142 and the detector 146. An example of a single radiograph 160 is shown in FIG. 2. The radiograph 160 and all radiographs described herein are understood to be digital. In one embodiment, a series of 720 images can be collected as the object 146 is rotated in place between the source 142 and the detector 148. In other embodiments, more images or fewer images may be collected as will be understood by those skilled in the art. In some embodiments, radiographs can be referred to as projection images.

Figure 3:
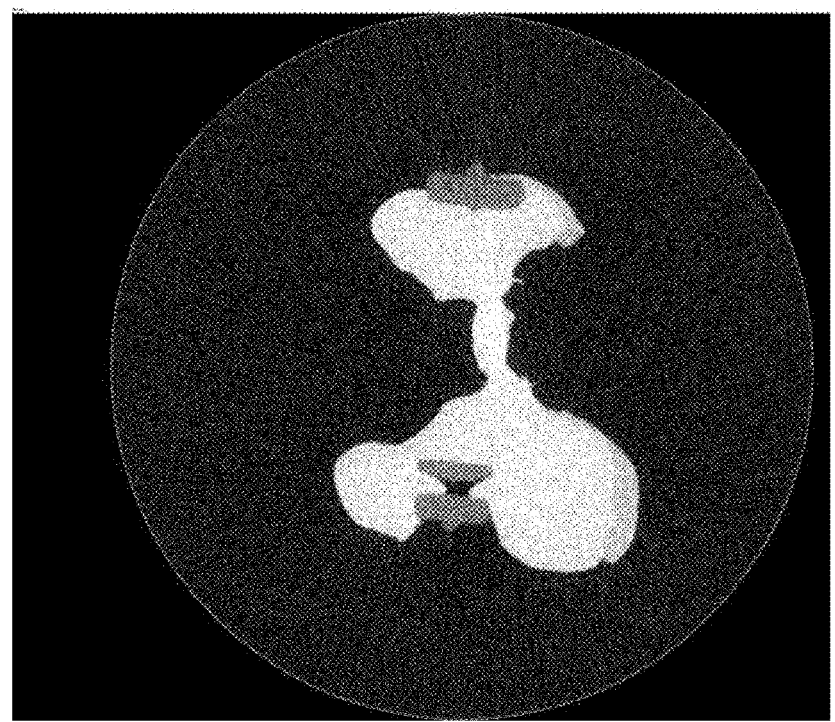
FIG. 3 shows a cross-section of a 3-dimensional (3D) volumetric image.

The plurality of radiographs 160 of the object 146 are generated by and stored within a storage medium contained within the processor 150 of the scanning system 140, where they may be used by software contained within the processor to perform additional operations. For example, in an embodiment, the plurality of radiographs 160 can undergo tomographic reconstruction in order to generate a 3D virtual image 170 (see FIG. 3) from the plurality of 2D radiographs 160 generated by the scanning system 140. In the embodiment shown in FIG. 3, the 3D virtual image 170 is in the form of a volumetric image or volumetric density file (shown in cross-section in FIG. 3) that is generated from the plurality of radiographs 160 by way of a CT reconstruction algorithm associated with the scanning system 140. In some embodiments, the object being scanned can be a physical dental impression. For example, the object 146 being scanned be a triple tray dental impression. In some embodiments, the object 146 can be a single or double full arch impression. A physical dental impression typically includes an impression material placed on a rigid body, which is inserted into a person's mouth. Any other CT scanning system known in the art can be used in some embodiments.

In some embodiments, a computer-implemented method of compressing CT reconstruction images can include: receiving a volumetric density file including one or more voxels; replacing one or more voxel density values below an air density value with the air density value; replacing one or more voxel density values above a material density value with the material density value; determining one or more voxels of interest; replacing one or more non-interesting voxel density values below a material surface density with the air density value; replacing one or more non-interesting voxel density values above the material surface density with the material density value; quantizing all voxels to provide a reduced volume image; and compressing the reduced volume image to provide a compressed volume image.

Figure 4:
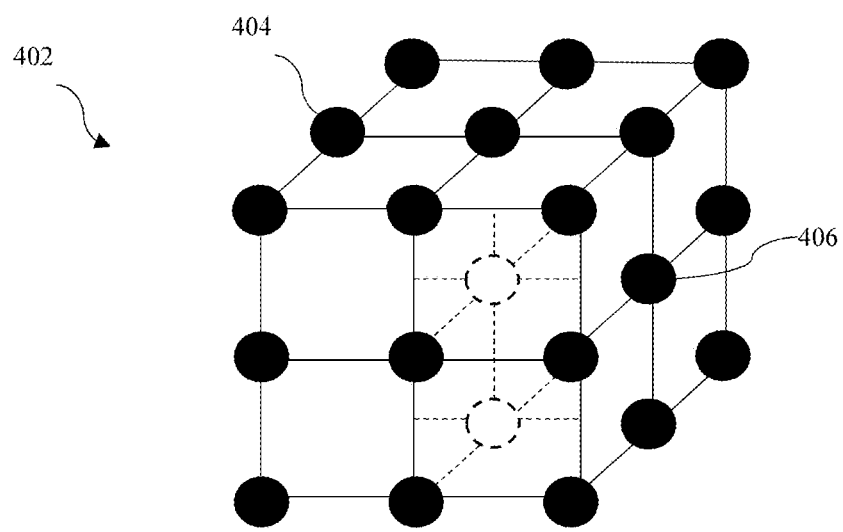
FIG. 4 is a perspective view of an illustration of a 3D volumetric image.

In some embodiments, the computer-implemented method can include receiving a volumetric density file that has one or more voxels. FIG. 4 illustrates an example of at least a portion of a volumetric density file 402 that includes one or more voxels such as voxel 404 and voxel 406. CT-reconstructed volumetric images for modern day scanners typically have dimensions 2000×2000×2000 or even higher. Only a few voxels are shown in the illustration of FIG. 4 for simplicity. In reality, the volumetric density file can contain many thousands of voxels. Each voxel can include density information at the x-y-z position in the volumetric density file in which it is positioned. For example, voxel 404 can have a density value of 1.0 at its x-y-z position in the volumetric density file 402, and voxel 406 can have a density value of 0.1 at its x-y-z position in the volumetric density file 402, for example. In some embodiments the volumetric density file is of a CT scanned physical dental impression. In some embodiments the physical dental impression can include an impression material that has a material density value. Densities of materials are known in the art, and can be ascertained and used as the material density.

In some embodiments, the computer-implemented method can determine the air density value and the material density value in the volumetric density file. In some embodiments, the computer-implemented method can determine the air density value and the material density value based on a value set by a user or another program for each. In some embodiments the air density value and/or material density value are configurable. For example, in some embodiments the air density value and/or material density value can be set by a user using an input device via a graphical user interface or other input interface, for example. In some embodiments, the air density value and/or material density value can be set by a user or another program in a configuration file that can be read by the computer-implemented method.

In some embodiments the air density value and/or material density value can be determined automatically. One example is described in PROCESSING CT SCAN OF DENTAL IMPRESSION, U.S. patent application Ser. No. 16/451,315 of Nikolskiy et al., the entirety of which is hereby incorporated by reference. For example, in some embodiments the air density value and/or the material density value can be determined from a density frequency distribution. The number of voxels at a particular density value can represent the amount of the material/air having that particular density. In some scans, air occupies most of the CT scan volume. This can occur, for example, in CT scans of smaller objects whose volume is less than the volume of air in the CT scan volume. For example, in the case of physical dental impressions containing impression material, this can include triple tray impressions or other dental impressions that occupy a smaller volume of the CT scan volume than air. In such scans, since air has the highest volume, the number of voxels with a density value falling within the density range of air is highest. In some embodiments, the impression material occupies the second highest volume in the CT scan volume next to air. The number of voxels having a density falling within the density range of the impression material can therefore be the second highest. Similarly, other materials such as a handle can constitute the least amount of material and therefore occupy the least volume in the CT scan volume. The number of voxels having a density falling within the density range of the handle material or other non-impression material of the physical dental impression can therefore have the lowest voxel count. In another example, the object being scanned can occupy most of the CT scan volume. For example, in the case of a physical dental impression, the dental impression material can occupy most of the CT scan volume. This can occur in CT scans of full arch impressions, for example, or other dental impressions that occupy more of the CT scan volume than air. In such scans, the impression material of the dental impression can occupy the most volume in the CT scan volume. The number of voxels having a density value falling within the density range of the impression material can therefore be the highest voxel count. The air in such a scan can occupy the second highest volume in the CT scan volume. The number of voxels having a density falling within the density range of air can therefore be the second highest voxel count. Similarly, other materials such as the handle of the physical dental impression can constitute the least amount of material in the CT scan so that the number of voxels having a density falling within the density range of the handle material can have the lowest voxel count.

The volumetric density file contains voxels having density information of one or more materials and surrounding air in a CT scan volume of an object such as a physical dental impression. As illustrated in the histogram 211 of FIG. 5(a), in some embodiments, the computer-implemented method can generate a density frequency distribution of the volumetric density file. In some embodiments, the histogram is a pair of numbers such as density value and the number of voxels with the density in between the density value and a next density value. The computer-implemented method can, for example, subdivide the range from minimal voxel value to maximal voxel value on 256 intervals (or bins).

The histogram 211 is shown for illustrative purposes and includes an x-axis 213 of density values and the y-axis 214 of the number of voxels (voxel counts), for example. All histograms illustrating the density frequency distribution herein include an x-axis of density values and a y-axis of the number of voxels (voxel counts). The computer-implemented method can receive a volumetric density file. The computer-implemented method can generate a normalized scan density range 201 for the volumetric density file. For example, in some embodiments, the computer-implemented method can generate the normalized scan density range 201 to be between 0.0 and 1.0. The computer-implemented method can subdivide the normalized scan density range into one or more scan density subranges 203 (scan density subrange 203 is shown among multiple scan density subranges in a magnified view). For example, the computer-implemented method can subdivide the normalized scan density range 201 of 0.0 and 1.0 into multiple scan density subranges 203. In some embodiments, the number of scan density subranges 203 can be 500, for example. In some embodiments, more or fewer scan density subranges 203 are possible. For each voxel, the computer-implemented method can normalize the density value of the voxel to fall within the normalized scan density range 201. The computer-implemented method can compare the normalized density of the voxel with the one or more scan density subranges 203 and can increment the voxel count for the scan density subrange 203 within which the normalized voxel density value falls. The computer-implemented method can load the next voxel from the volumetric density file and repeats the process for every voxel in the volumetric density file to determine the total voxel count for each of the scan density subranges 203. In some embodiments, the computer-implemented method can take a logarithm of the voxel counts for each scan density subrange 203. The computer-implemented method in this manner can generate the density frequency distribution which is depicted as histogram 211 for illustrative purposes.

In some embodiments, the computer-implemented method can determine the air density range and the particular material density range based on voxel counts in the density frequency distribution. In some embodiments, the computer-implemented method can use voxel counts to determine one or more voxel count peaks as the highest voxel counts in the density frequency distribution. For example, the computer-implemented method can compare the voxel counts at each scan density subrange and determine which scan density subrange the voxel count either switches from increasing to decreasing, or begins decreasing. In some embodiments, a voxel count peak can span one or more scan density subranges. Other techniques can be used to determine voxel count peaks in the density frequency distribution. In some embodiments, the computer-implemented method can determine valleys by determining the scan density subranges the voxel count either switches from decreasing to increasing, or starts increasing. Other techniques can be used to determine valleys in the density frequency distribution. In some embodiments, a voxel count peak can span one or more scan density subranges. In some embodiments, the number of peaks in the density frequency distribution is proportional to the number of materials plus air in the CT scan volume, for example. In some embodiments, the valleys are arranged between two voxel count peaks.

For example, as illustrated in FIG. 5(a), the computer-implemented method can generate a density frequency distribution which is illustrated in the histogram 211. The computer-implemented method can determine a highest voxel count peak 216, second highest voxel count peak 220, and third voxel count peak 218, for example. Additional voxel count peaks can also be present and determined by the computer-implemented method. As discussed previously, highest voxel count peak 216, second highest voxel count peak 220, third voxel count peak 218 and any other peaks herein can span one or more scan density subrange(s). In some embodiments, the computer-implemented method determines a first valley 230 as the shortest height or least voxel count between the highest voxel count peak 216 and the second highest voxel count peak 220, and a second valley 233 as the shortest height or least voxel count between the second highest voxel count peak 220 and the third highest voxel count peak 218. Each valley can span one or more scan density subrange(s). The valleys can define a highest peak density range 231, a second highest peak density range 234, and a lowest peak density range 232, for example.

In some embodiments, the computer-implemented method can determine one or more material and air density ranges based on the type of impression scanned. In some cases, most of the CT scan volume can be air, followed by the volume of a particular material whose digital surface is desired, such as impression material, for example, followed by the volume other materials, such as the handle material in some embodiments, for example. In such cases, the air density range can correspond to the highest peak density range and the particular material density range can correspond to the second highest peak density range, for example. In other cases, most of the CT scan volume can be the particular material whose digital surface is desired, followed by air, followed by other materials, such as the handle material, for example. In such cases, the particular material density range can correspond to the highest peak density range and the air density range can correspond to the second highest peak density range, for example.

Figure 5B:
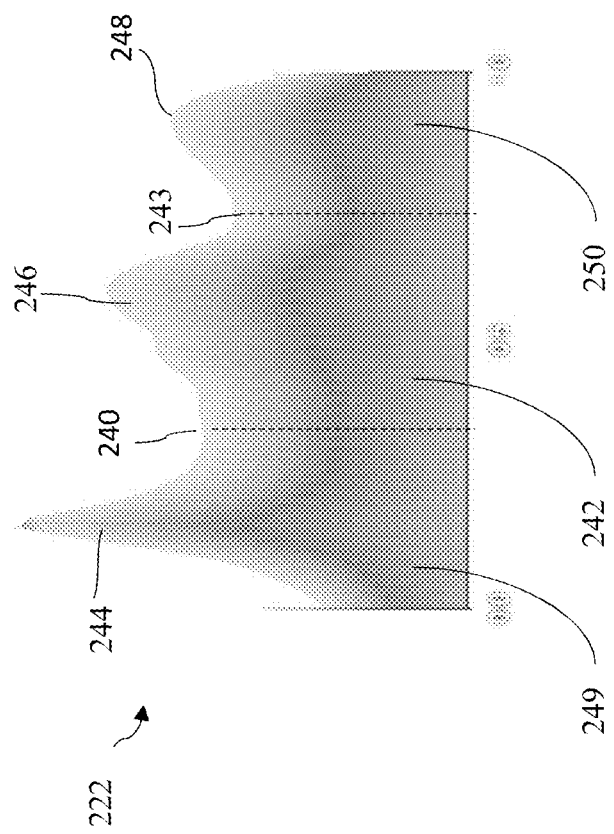

In some embodiments, total voxel counts in the density ranges can be used instead of voxel count peaks to determine an iso-value of density between the air density range and the particular material density range. For example, as illustrated in the example of FIG. 5(b), the computer-implemented method can generate a density frequency distribution 222 as described previously, the computer-implemented method determines voxel count peaks 244, 246, and 248 and valleys 240 and 243, thereby establishing density ranges between density value 0.0 and density value at first valley 240, between density value at first valley 240 and density value at second valley 243, and between density value at second valley 243 and the maximum normalized density value. In this example, the maximum normalized density value is 1.0, for example. The computer-implemented method can determine the total number of voxels between density value 0.0 and the first valley 240 as total voxel count 249, between the first valley 240 and the second valley 243 as total voxel count 242, and the total number of voxels after the second valley 243 as total voxel count 250. In this example, if the computer-implemented method receives information that the dental impression type is a triple tray, then the computer-implemented determines that the highest voxel count density range will correspond to air. For example, if the total voxel count 249 is the highest voxel count density range, then the computer-implemented method determines that the density range between 0.0 and the first valley 240 as an air density range. If the total voxel count 242 is the second highest voxel count density range for example, then the computer-implemented method determines that the density range between the first valley 240 and the second valley 243 is the particular material density range.

In some embodiments, the computer-implemented method receives a volumetric density file and generates a density frequency distribution. The computer-implemented method can receive information regarding whether air or the object occupies the greatest volume in the CT scan volume. This information can be provided in a user editable configuration file, for example, or by the user through an input device. For example, in some embodiments, the computer-implemented method can receive information regarding type of impression scanned (triple tray or full arch). The computer-implemented method can determine whether air or the particular material occupies the most volume of the CT scan volume based on the volume information of the object being scanned. In some embodiments, the computer-implemented method can determine air occupies the most volume if the impression type is a triple tray impression, for example. In some embodiments, the computer-implemented method can determine the particular material occupies the most volume if the impression type is a full arch impression, for example.

In some embodiments, the computer-implemented method can determine voxel count peaks in the density frequency distribution. If the computer-implemented method determines that air occupies most of the CT scan volume and the particular material occupies the second highest volume based on the type of impression scanned, the computer-implemented method can determine the air density range as the one or more density subranges of the highest voxel count peak (or the density range with the highest total voxel count) and the particular material density range as the one or more density subranges of second highest voxel count peak (or the density range with the second highest total voxel count). If the computer-implemented method determines that a particular material occupies most of the CT scan volume and air occupies the second most based on the type of impression scanned, the computer-implemented method can determine the particular material density range as the one or more density subranges of the highest voxel count peak (or the density range with the highest total voxel count) and the air density range as the one or more density subranges of the second highest peak (or the density range with the second highest total voxel count).

In some embodiments, the computer-implemented method can replace one or more voxel density values below the air density value with the air density value, and replace one or more voxel density values above the material density value with the material density value. In the example of FIG. 4, if voxel 404 is above the material density value, then the computer-implemented method can replace the voxel 404 density value with the material density value. If the density value of voxel 406 is below the air density value, then the computer-implemented method can replace the voxel 406 density value with the air density value.

In some embodiments, the computer-implemented method can determine one or more voxels of interest. In some embodiments, the one or more voxels of interest can include one or more material surface voxels. In some embodiments, the material can be the impression material, and the material surface voxels can be impression material surface voxels. In some embodiments the one or more material surface voxels can be one or more voxels having immediate neighbors with density values above and below a material surface density. In some embodiments, the immediate neighbors can include six immediate neighbors. In some embodiments the material surface density is determined as $$d=(\text{air density}+\text{material density})/2.$$

Figure 6:
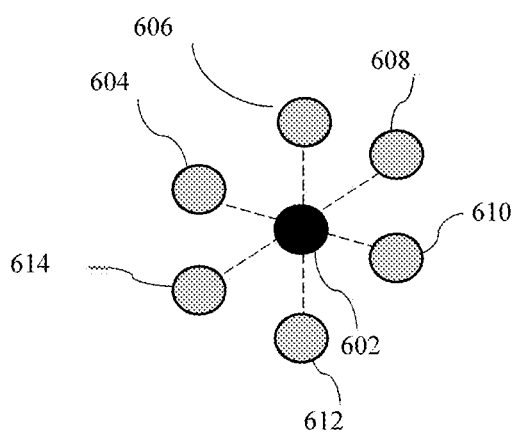
FIG. 6 is a perspective view of a portion of a 3D volumetric density file.
Figure 6:
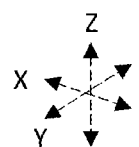

FIG. 6 is an example illustrating a portion of a volumetric density file. The computer-implemented method can determine whether a particular voxel such as particular voxel 602 is part of the material surface by comparing the density values of its neighboring voxels such as first neighboring voxel 604, second neighboring voxel 606, third neighboring voxel 608, fourth neighboring voxel 610, fifth neighboring voxel 612, and sixth neighboring voxel 614. If, for example, first neighboring voxel 604 has a density value above the material surface density value and fifth neighboring voxel 612 has a density value below the material surface density value, then the computer-implemented method determines that particular voxel 602 is a material surface voxel. On the other hand, if all of the neighboring voxels are above or below the material surface density value, then the computer-implemented method determines that the particular voxel 602 is not a material surface voxel.

In some embodiments, the computer-implemented method can optionally further determine voxels of interest as one or more voxels within a fixed distance of each established material surface voxel. In some embodiments the fixed distance is a configurable value. For example, in some embodiments the fixed distance can be set by a user using an input device via a graphical user interface or other input interface, for example. In some embodiments, the fixed distance can be set by a user or another program in a configuration file that can be read by the computer-implemented method. In some embodiments, points within a fixed distance can be determined in 3 dimensions from FixedDistance[{a,b,c},{x,y,z}]=abs [a−x]+abs [b−y]+abs [c−z].

Figure 7:
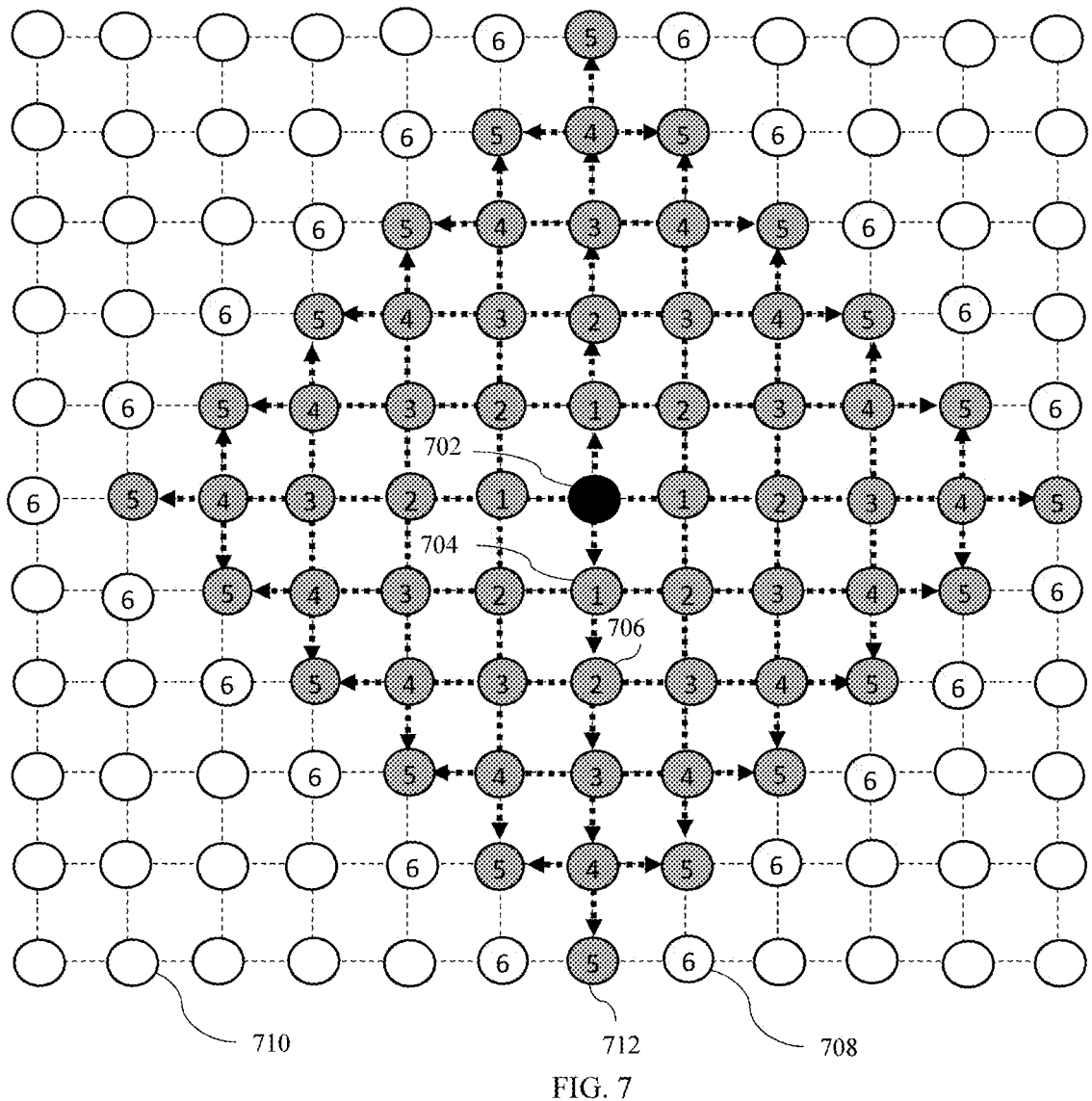
FIG. 7 is a 2 dimensional view of an illustration of a 3D volumetric density file.

In some embodiments the fixed distance can be 5 voxels, for example. However, any other number of voxels can be used for the fixed distance. FIG. 7 illustrates an example of determining additional voxels of interest when the fixed distance set to 5 voxels. FIG. 7 is an illustration of a 2D view of a 3D volumetric density file with one or more voxels such as established material surface voxel 702. As discussed previously, the established material surface voxel 702 can be determined as being a material surface voxel. The computer-implemented method can, based on the fixed distance value determine 5 neighboring voxels as also belonging to the material surface and also as voxels of interest. All voxels within 5 voxels of the established material surface voxel 702 are shown with their voxel distance from the established material surface voxel 702. The computer-implemented method can start with a neighboring voxel and count it as the first voxel and include every voxel connected in every connected direction from the neighboring voxel within 5 voxels. For example, the computer-implemented method can start with a neighboring voxel such as first neighboring voxel 704 and count it as the first voxel. From there, the computer-implemented method can count up to 4 voxels in every connected direction from the first neighboring voxel 704. Next, the computer-implemented method can start with a neighbor 706 of the first neighboring voxel 704 and count up to 3 voxels in every connected direction since the first neighboring voxel 704 counts as a first voxel and its neighbor, neighbor 706 counts as the second voxel. For example, the computer-implemented method can determine the shaded voxels in the figure as also being voxels of interest since they are 5 voxels from the established material surface voxel 702 through neighboring voxel connections. The computer-implemented method can repeat the process for every neighbor in 3D of one or more established material surface voxels. For example, the same process can be repeated in the x-y plane, the x-z plane, and the y-z plane of the 3D volumetric density file for one or more established material surface voxels.

In some embodiments, non-interesting voxels can include voxels not belonging to the material surface. In some embodiments, non-interesting voxels can also include voxels not within the fixed distance of each established material surface voxel, for example. In some embodiments, non-interesting voxels can include all voxels that are not of interest. In some embodiments, the computer-implemented method can replace one or more non-interesting voxel density values below the material surface density with the air density value. For example, if a first non-interesting voxel 708 has a density value below the material surface density, then the computer-implemented method can in some embodiments replace the density value of non-interesting voxel 708 with the air density value. In some embodiments, the computer-implemented method can replace one or more non-interesting voxel density values above the material surface density with the material density value. For example, if a second non-interesting voxel 710 has a density value above the material surface density value, then the computer-implemented method can replace the density value of the second non-interesting voxel 710 with the material density value. In some embodiments, the densities of voxels of interest are not adjusted based on the material surface density value d. For example, material surface voxel 712 is a voxel of interest, and is therefore not adjusted based on the material surface density value d. In some embodiments, the result can be all voxels of interest retaining their density value, and all non-interesting voxel density values being replaced with values of either air density or material density.

In some embodiments, the computer-implemented method can scale the densities of all voxels to fall within the [0,1] range, inclusive of 0 and 1 for example. In some embodiments, the computer-implemented method can quantize all voxels to provide a reduced volume image. In some embodiments quantizing can include a lower bit-count than 16 bits per voxel. In some embodiments the lower bit-count is 8 bits per voxel. In some embodiments, quantizing can include, for example, the following: given a value in between 0 and 1, multiply the value on 255 (which is 2 in the power of 8 minus 1, to quantize to 8 bits). Next, round the multiplied value to the nearest integer, which provides an integer in between 0 and 255. Next, binary code the integer in 8 bits. In some embodiments, the value 0 can represent air density (do), and the value 255 (maximum possible 8 bit value) can represent material density (di), and all other values between 0 and 255 can represent intermediate quantities between the air density and the material density, for example. In some embodiments, the resulting voxels of interest (i.e. material surface voxels) can be in the range of 0 to 255, and the non-material voxels can be either 0 or 255.

In some embodiments, the computer-implemented method can compress the reduced volume image to provide a compressed volume image. In some embodiments the compressing can include applying conventionally available lossless compression to the reduced volume image. In some embodiments, the computer-implemented method can invoke a conventionally available lossless compression program. In some embodiments the computer-implemented method can implement lossless compression using any conventionally available lossless compression such as, for example, LZMA. One example of the LZMA algorithm is described in HARDWARE IMPLEMENTATION OF LZMA DATA COMPRESSION ALGORITHM, by E. Jebamalar Leavline and D. Asir Antony Gnana Singh, International Journal of Applied Information Systems (IJAIS)—ISSN: 2249-0868, Foundation of Computer Science FCS, New York, USA, Volume 5—No. 4, March 2013, the entirety of which is hereby incorporated by reference. Other types of compression known in the art can be used.

In some embodiments, LZMA compression as known in the art and as implemented by the computer-implemented method can include, for example, utilizing dictionary compression, and then encoding the output using a range encoder that utilizes probability prediction of every bit. The dictionary compression can generate a stream of literal symbols and phrase references by finding matches, and the range encoder can encode one bit at a time. The LZMA compression can code former content byte sequences instead of the original data. In some embodiments, the computer-implemented method code can include, for example: address to previously coded content, sequence length, first deviating symbol. In cases where no identical byte sequence exists in previously coded content, the computer-implemented method can set the address to zero, the sequence length to zero, and code a new symbol. LZMA as is known in the art can use delta encoding, in which a delta filter can store/send data as differences between sequential data instead of entire files. The output of the first byte can be the data stream, and subsequent bytes can be stored as the difference between the current and previous byte. The computer-implemented method can implement LZMA as known in the art by utilizing a sliding dictionary such as an adaptive dictionary. The sliding dictionary implementation can include receiving input data for compression, building the source tree, determining the best match, beginning recursion, and updating the tree with new scanned symbols, for example. In some implementations, the oldest branches can be cleaned up. In some embodiments, the computer-implemented method can perform range encoding by encoding all symbols in the message into a single number. In range encoding, the computer-implemented method can for a large integer range and a probability estimation of the symbols, divide an initial range into one or more sub-ranges having sizes proportional to the probability of the symbol, and encode each symbol by reducing a current range to only a sub-range corresponding to a next symbol to be encoded.

In some embodiments the compression can include multi-threaded compression. In some embodiments, multi-threaded compression can be performed by dividing the file into separate pieces which can be distributed to separate threads, where each thread is encoded separately, for example. Multi-threaded compression can be performed using LZMA2/XZ, which is conventionally known in the art, for example. The XZ LZMA2 encoder can process input in pieces (the lower of up to 2 MB uncompressed, or 64 k compressed). The computer-implemented method can provide each piece to the LZMA encoder and then output the shorter of the LZMA2 LZMA piece that includes the encoded data, or the LZMA2 uncompressed piece. The computer-implemented method can reset the LZMA state only in the first block if there is a change of properties request and each time a compressed piece is output. The computer implemented method can change the LZMA properties only in the first block, or if there is a request for a change of properties. The computer-implemented method resets the dictionary only in the first block.

In some embodiments, before LZMA2 encoding, the computer-implemented method can XZ encoding by applying a BCJ filter to filter executable code and replacing relative offsets with absolute values which are repetitive. The computer-implemented method can alternatively apply the delta filter as described previously prior to LZMA2 encoding.

In some embodiments, the computer-implemented method can optionally include providing a histogram with the compressed volume image. For example, in some embodiments, the computer-implemented method can add the frequency distribution/histogram to the reduced volume image data and then compress the data. In some embodiments, a compressed reconstruction can be single file that can include a header with metadata (e.g. scanner name, resolution, volume dimension, etc.), and compressed histogram pairs. In some embodiments, the compressed reconstruction can be a single file that can include a header with metadata, the histogram before compression and compressed voxels themselves.

In some embodiments, the computer-implemented method can optionally upload the compressed volume image to a remote system such as cloud-based system, for example, to extract a digital surface of the scanned object. In some embodiments, the upload can be performed manually by a user using an input device or performed automatically, such as through an automated process. In some embodiments, the remote or cloud-based system can include one or more computing systems that can be connected together by a network.

In some embodiments, one or more remote programs running on the remote or cloud-based system can receive the compressed volume image and use decompression to extract the reduced volume image data and/or histogram/frequency distribution information. In some embodiments, the decompression type can be any type known in the art, and can correspond to the compression type used.

For example, in some embodiments, the decompression can be of LZMA and LZMA2/XZ compressed files as is known in the art. In some embodiments, a computer-implemented decompression method can decompress the LZMA2/XZ compressed files. In some embodiments, the LZMA can be decoded by bit by a range decoder.

In some embodiments, computer-implemented decompression method can perform normalization as follows in some embodiments:
1. Shift left by 8 bits, range and code.
2. Read one byte from compressed stream
3. Set least significant 8 bits of code=the read byte value.

In some embodiments, the computer-implemented decompression method can be context based. The context can be the predicted probability of the bit being zero, which can be read and updated by the range decoder. In some embodiments, the computer-implemented method initializes the probability to $2^{10}$, which can represent 0.5 probability.

In some embodiments, the computer-implemented method can perform context-based range decoding of a bit using the probability variable as follows:

```
1.   If range < 2^24, then do normalization
2.   Set bound = floor(range / 2^11) * probability
3.   If code < bound: {
     Set range = bound;
     Set probability = (probability + floor((2^11 - prob) / 2^5));
     Return bit zero;}
4.      Else if code >= bound: {
     Set range = range - bound;
     Set code = code - bound;
     Set prob = (prob - floor(prob / 2^5));
     Return bit 1;}
```

In some embodiments, the computer-implemented method can perform fixed-probability range decoding of a bit as follows:

| | |
|---|---|
| 1. | If range is less than 2^24, perform normalization |
| 2. | Set range to floor(range / 2) |
| 3. | If code is less than range:{ <br> Return bit 0;} |
| 4. | Else if code >= range): { <br> Set code to code − range; <br> Return bit 1;} |

In some embodiments, the computer-implemented decompression method can use a fixed probability range. In such a case, the computer-implemented decompression method assumes a 0.5 probability.

Figure 8:
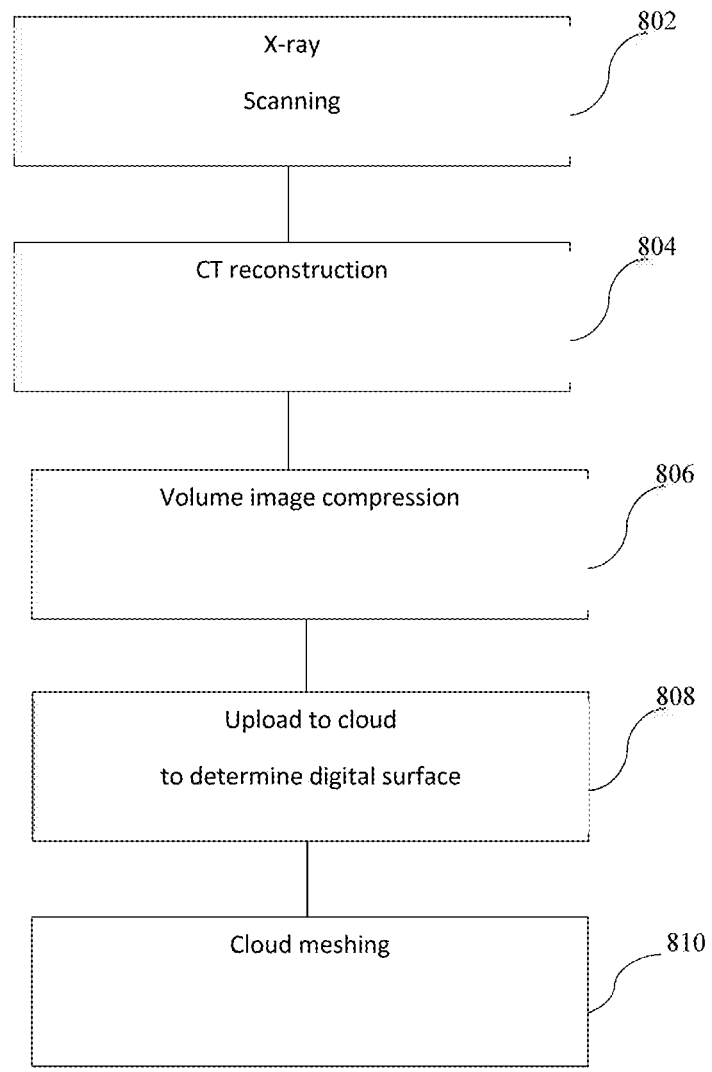
FIG. 8 is a flowchart of an example workflow incorporating volume image compression and cloud-based digital surface determination.

In some embodiments, the one or more programs can process the reduced volume image data and/or histogram/frequency distribution information to extract a digital surface of the scanned object and generate a 3D digital model, for example, that can include a digital surface mesh. One example of determining the digital surface of the scanned object can be found in PROCESSING CT SCAN OF DENTAL IMPRESSION, U.S. patent application Ser. No. 16/451,315 of Nikolskiy, et al. Another example of determining the digital surface of the scanned object can include Marching Cubes, or other digital model generation methods and techniques known in the art. An example of the conventional Marching Cubes is described in SYSTEM AND METHOD FOR THE DISPLAY OF SURFACE STRUCTURES CONTAINED WITHIN THE INTERIOR REGION OF A SOLID BODY, U.S. Pat. No. 4,710,876 assigned to General Electric Co., the entirety of which is hereby incorporated by reference. In some embodiments, programs implementing these or other digital surface determination methods can operate on one or more computing systems remote to the processor 150 from FIG. 1, including, but not limited to cloud-based systems, for example. Digital surface determination can thus advantageously be offloaded from the processor 150 in FIG. 1. FIG. 8 illustrates an example of a workflow incorporating volume image compression and cloud-based digital surface determination. A CT scanning system can perform x-ray scanning at 802 and CT reconstruction of the volumetric density file at 804. The computer-implemented method can perform volumetric image compression at 806 and then upload the compressed volumetric density file to a cloud to determine the digital surface at 808. The cloud can perform digital surface determination (meshing) at 810.

In some embodiments, the computer-implemented method can perform decompression. In some embodiments, another program can perform decompression. In some embodiments, the decompression can be performed locally such as, for example on the same computing system and/or processor 150. In some embodiments, the computer-implemented method or other program can load and decompress from storage attached to a computing environment directly or through a network connection.

Figure 9:
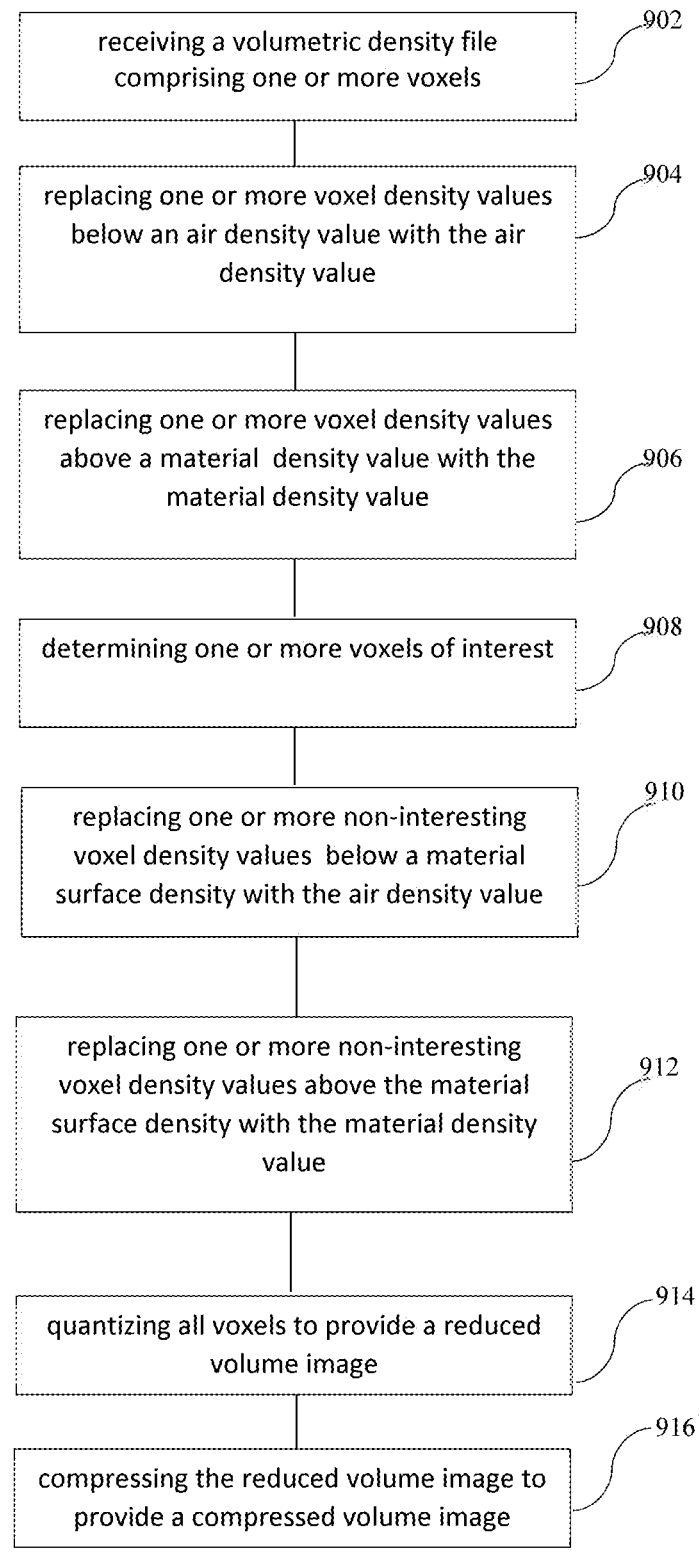
FIG. 9 is a flowchart of an example of a computer-implemented method of compressing CT reconstruction images in some embodiments.

FIG. 9 illustrates an example of a computer-implemented method of compressing CT reconstruction images in some embodiments. The computer-implemented method can include: receiving a volumetric density file including one or more voxels at 902; replacing one or more voxel density values below an air density value with the air density value at 904; replacing one or more voxel density values above a material density value with the material density value at 906; determining one or more voxels of interest at 908; replacing one or more non-interesting voxel density values below a material surface density with the air density value at 910; replacing one or more non-interesting voxel density values above the material surface density with the material density value at 912; quantizing all voxels to provide a reduced volume image at 914; and compressing the reduced volume image to provide a compressed volume image 916.

Some embodiments can include a system of compressing CT reconstruction images, which can include: a processor, a computer-readable storage medium including instructions executable by the processor to perform steps including: receiving a volumetric density file including one or more voxels; replacing one or more voxel density values below an air density value with the air density value; replacing one or more voxel density values above a material density value with the material density value; determining one or more voxels of interest; replacing one or more non-interesting voxel density values below a material surface density with the air density value; replacing one or more non-interesting voxel density values above the material surface density with the material density value; quantizing all voxels to provide a reduced volume image; and compressing the reduced volume image to provide a compressed volume image.

The computer-implemented method, system, and instructions on non-transitory computer readable medium can optionally include the following features in various combinations in some embodiments: the volumetric density file is of a CT scanned physical impression. The physical impression can include an impression material. The one or more material surface voxels can include one or more voxels having immediate six neighbors with density values above and below a material surface density. The material surface voxels can further include one or more voxels within a fixed distance of each material surface voxel. The fixed distance can be 5 voxels. Quantizing can include a lower bit-count than 16 bits per voxel. The lower bit-count can be 8 bits per voxel.

In some embodiments, the computer-implemented method can, for example, prepare a density frequency distribution/histogram, determine air peak and material peak from the histogram, set densities below air density to the air density value and voxel densities above the material density to the material density, find voxels of interest (for example—within distance 5 voxels) from approximate position of the impression surface, replace all densities outside of voxels of interest with either air density or material density, scale the remaining densities into [0,1] range, discretize them to 8 bit, and apply lossless compression.

One or more advantages of one or more features can include, for example, improved size reduction and/or compression. One or more advantages of one or more features can include, for example, efficiently compressing volumetric density files. One or more advantages of one or more features can include, for example, approximately 100× compression ratios of volumetric density files. One or more advantages can include of one or more features can include, for example, reduction of the amount of data to be transferred from many gigabytes to dozens of megabytes. One or more advantages can include of one or more features can include, that the smaller sized volumetric density file can be increased portability, since the smaller file sizes can allow fast transfer of the volumetric density file to another machine or location. One or more advantages can include of one or more features can include, for example, reduced storage requirements. This can allow, for example, storage of more volumetric density files in one location. One or more advantages can include of one or more features can include, for example, that compressed volumetric density files can be stored for a long time, whereas uncompressed ones can be too large for permanent storage. One or more advantages can include of one or more features can include, for example, that the compression itself takes just a few seconds. One or more advantages of one or more features can include, for example, the ability to use cloud meshing, which can utilize resources only when data is being processed instead of a few local machines for generating the digital model and surface mesh. One or more advantages of one or more features can include, for example, storing data for only a subset of voxels of the volumetric density file. One or more advantages of one or more features can include, for example, faster encoding of a subset of voxels of the volumetric density file versus encoding the entire volumetric density file. One or more advantages of one or more features can include, for example, automation of compression of CT reconstructed images, which can improve efficiency and reduce errors, for example. One or more advantages of one or more features can include, for example, lossy CT compression, which can reduce or prevent errors from being introduced into the CT reconstructed images.

Figure 10:
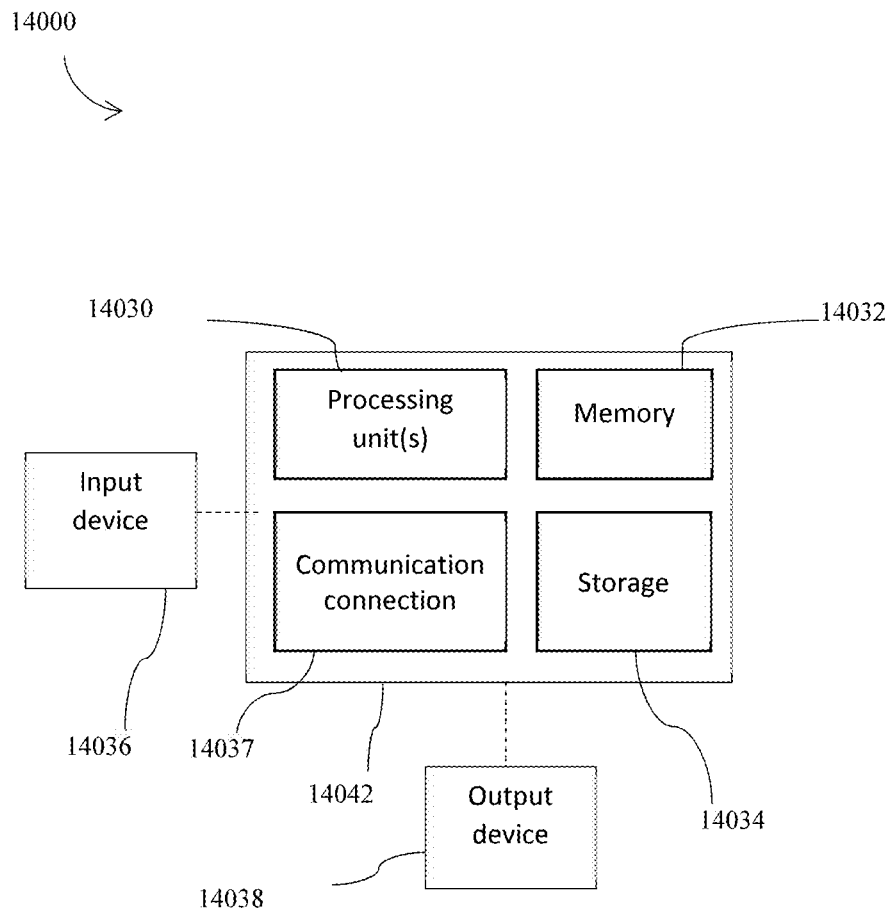
FIG. 10 is a diagram of a system in some embodiments.

FIG. 10 illustrates a processing system 14000 in some embodiments. The system 14000 can include a processor 14030, computer-readable storage medium 14034 having instructions executable by the processor to perform one or more steps described in the present disclosure.

One or more of the features disclosed herein can be performed and/or attained automatically, without manual or user intervention. One or more of the features disclosed herein can be performed by a computer-implemented method. The features—including but not limited to any methods and systems—disclosed may be implemented in computing systems. For example, the computing environment 14042 used to perform these functions can be any of a variety of computing devices (e.g., desktop computer, laptop computer, server computer, tablet computer, gaming system, mobile device, programmable automation controller, video card, etc.) that can be incorporated into a computing system comprising one or more computing devices. In some embodiments, the computing system may be a cloud-based computing system.

For example, a computing environment 14042 may include one or more processing units 14030 and memory 14032. The processing units execute computer-executable instructions. A processing unit 14030 can be a central processing unit (CPU), a processor in an application-specific integrated circuit (ASIC), or any other type of processor. In some embodiments, the one or more processing units 14030 can execute multiple computer-executable instructions in parallel, for example. In a multi-processing system, multiple processing units execute computer-executable instructions to increase processing power. For example, a representative computing environment may include a central processing unit as well as a graphics processing unit or co-processing unit. The tangible memory 14032 may be volatile memory (e.g., registers, cache, RAM), non-volatile memory (e.g., ROM, EEPROM, flash memory, etc.), or some combination of the two, accessible by the processing unit(s). The memory stores software implementing one or more innovations described herein, in the form of computer-executable instructions suitable for execution by the processing unit(s).

A computing system may have additional features. For example, in some embodiments, the computing environment includes storage 14034, one or more input devices 14036, one or more output devices 14038, and one or more communication connections 14037. An interconnection mechanism such as a bus, controller, or network, interconnects the components of the computing environment. Typically, operating system software provides an operating environment for other software executing in the computing environment, and coordinates activities of the components of the computing environment.

The tangible storage 14034 may be removable or non-removable, and includes magnetic or optical media such as magnetic disks, magnetic tapes or cassettes, CD-ROMs, DVDs, or any other medium that can be used to store information in a non-transitory way and can be accessed within the computing environment. The storage 14034 stores instructions for the software implementing one or more innovations described herein.

The input device(s) may be, for example: a touch input device, such as a keyboard, mouse, pen, or trackball; a voice input device; a scanning device; any of various sensors; another device that provides input to the computing environment; or combinations thereof. For video encoding, the input device(s) may be a camera, video card, TV tuner card, or similar device that accepts video input in analog or digital form, or a CD-ROM or CD-RW that reads video samples into the computing environment. The output device(s) may be a display, printer, speaker, CD-writer, or another device that provides output from the computing environment.

The communication connection(s) enable communication over a communication medium to another computing entity. The communication medium conveys information, such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Any of the disclosed methods can be implemented as computer-executable instructions stored on one or more computer-readable storage media 14034 (e.g., one or more optical media discs, volatile memory components (such as DRAM or SRAM), or nonvolatile memory components (such as flash memory or hard drives)) and executed on a computer (e.g., any commercially available computer, including smart phones, other mobile devices that include computing hardware, or programmable automation controllers) (e.g., the computer-executable instructions cause one or more processors of a computer system to perform the method). The term computer-readable storage media does not include communication connections, such as signals and carrier waves. Any of the computer-executable instructions for implementing the disclosed techniques as well as any data created and used during implementation of the disclosed embodiments can be stored on one or more computer-readable storage media 14034. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, Python, JavaScript, Adobe Flash, or any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

In view of the many possible embodiments to which the principles of the disclosure may be applied, it should be recognized that the illustrated embodiments are only examples and should not be taken as limiting the scope of the disclosure.

What is claimed is:

1. A computer-implemented method of compressing CT reconstruction images, comprising:
    receiving a volumetric density file comprising one or more voxels, each comprising a voxel density value;
    replacing a first set of voxel density values below an air density value with the air density value;
    replacing a second set of voxel density values above a material density value with the material density value;
    quantizing all voxels of the one or more voxels to provide a reduced volume image; and
    compressing the reduced volume image to provide a compressed volume image.

2. The method of claim 1, wherein the volumetric density file is of a CT scanned physical impression.

3. The method of claim 2, wherein the physical impression comprises an impression material.

4. The method of claim 1, wherein a third set of voxels comprise one or more material surface voxels, the one or more material surface voxels comprising one or more voxels having immediate six neighbors with density values above and below a material surface density.

5. The method of claim 4, wherein material surface voxels further comprise one or more voxels within a fixed distance of each material surface voxel.

6. The method of claim 5, wherein the fixed distance is 5 voxels.

7. The method of claim 1, wherein quantizing comprises a lower bit-count than 16 bits per voxel.

8. The method of claim 7, wherein the lower bit-count is 8 bits per voxel.

9. A system of compressing computed tomography (CT) reconstruction images, comprising:
    a processor;
    a computer-readable storage medium comprising instructions executable by the processor to perform steps comprising:
        receiving a volumetric density file comprising one or more voxels, each comprising a voxel density value;
        replacing a first set of voxel density values below an air density value with the air density value;
        replacing a second set of voxel density values above a material density value with the material density value;
        quantizing all voxels of the one or more voxels to provide a reduced volume image; and
        compressing the reduced volume image to provide a compressed volume image.

10. The system of claim 9, wherein the volumetric density file is of a CT scanned physical impression.

11. The system of claim 10, wherein the physical impression comprises an impression material.

12. The system of claim 9, wherein one or more material surface voxels comprises one or more voxels having immediate six neighbors with density values above and below a material surface density.

13. The system of claim 12, wherein material surface voxels further comprise one or more voxels within a fixed distance of each material surface voxel.

14. The system of claim 13, wherein the fixed distance is 5 voxels.

15. The system of claim 9, wherein quantizing comprises a lower bit-count than 16 bits per voxel.

16. The system of claim 15, wherein the lower bit-count is 8 bits per voxel.

17. A non-transitory computer readable medium storing executable computer program instructions for compressing computed tomography (CT) reconstruction images, the computer program instructions comprising instructions for:
    receiving a volumetric density file comprising one or more voxels, each comprising a voxel density value;
    replacing a first set of voxel density values below an air density value with the air density value;
    replacing a second set of voxel density values above a material density value with the material density value;
    quantizing all voxels of the one or more voxels to provide a reduced volume image; and
    compressing the reduced volume image to provide a compressed volume image.

18. The medium of claim 17, wherein the volumetric density file is of a CT scanned physical impression.

19. The medium of claim 17, wherein a third set of voxels comprise one or more material surface voxels, comprises one or more voxels having immediate six neighbors with density values above and below a material surface density.

20. The medium of claim 19, wherein material surface voxels further comprise one or more voxels within a fixed distance of each material surface voxel.

* * * * *